(12) United States Patent
Naulet

(10) Patent No.: US 7,814,667 B2
(45) Date of Patent: Oct. 19, 2010

(54) DEVICE TO ASSIST IN QUANTIFYING A PRODUCT AND ITS USE

(75) Inventor: Thomas Naulet, Boulogne (FR)

(73) Assignee: Galderma S.A., Cham (CH)

( * ) Notice: Subject to any disclaimer, the term of this patent is extended or adjusted under 35 U.S.C. 154(b) by 1589 days.

(21) Appl. No.: 11/104,531

(22) Filed: Apr. 13, 2005

(65) Prior Publication Data
US 2006/0231571 A1 Oct. 19, 2006

(51) Int. Cl.
*G06G 1/08* (2006.01)
(52) U.S. Cl. .................................. 33/1 SD; 235/88 R
(58) Field of Classification Search ............... 33/1 SB, 33/1 SD, 494; 235/77, 78 R, 85 R, 88 R
See application file for complete search history.

(56) References Cited

U.S. PATENT DOCUMENTS

| | | | | |
|---|---|---|---|---|
| 3,690,547 A | * | 9/1972 | Eadon-Allen | 235/70 R |
| 3,747,847 A | * | 7/1973 | Cohen | 235/85 R |
| 4,117,315 A | * | 9/1978 | Ampt et al. | 235/88 R |
| 4,189,634 A | * | 2/1980 | LaBove et al. | 235/70 A |
| 4,308,450 A | * | 12/1981 | Ausman et al. | 235/70 A |
| 4,797,539 A | * | 1/1989 | Forest | 235/85 R |
| 4,882,472 A | * | 11/1989 | Sigman et al. | 235/88 R |
| 5,017,762 A | * | 5/1991 | Diamond | 235/78 R |
| 5,167,072 A | * | 12/1992 | Richardson | 33/1 SD |
| 5,678,862 A | * | 10/1997 | Hughes et al. | 283/65 |
| 6,484,932 B1 | * | 11/2002 | Kinney et al. | 235/73 |

FOREIGN PATENT DOCUMENTS

| | | | |
|---|---|---|---|
| EP | 99826 A2 | * | 2/1984 |
| EP | 114163 A1 | * | 8/1984 |
| FR | 2525366 A | * | 10/1983 |
| GB | 1437971 A | * | 6/1976 |
| GB | 1476668 A | * | 6/1977 |
| WO | WO 8606524 A1 | * | 11/1986 |

* cited by examiner

*Primary Examiner*—R. A. Smith
(74) *Attorney, Agent, or Firm*—Oblon, Spivak, McClelland, Maier & Neustadt, L.L.P.

(57) ABSTRACT

The invention relates to a device to assist in quantifying a medicament for application on the skin, characterized in that it includes, on the one hand, a first element having a first window and at least one additional window and, on the other hand, a second element having a first graduation and at least one additional graduation, each graduation comprising successive values, the said first and second elements being superimposed and mounted so as to rotate with respect to each other about an axis of rotation so that, when the second element is rotated with respect to the first element, each additional window is arranged in front of one of the successive values of each additional graduation, as a function of the position of the first window relative to the successive values of the first graduation. The invention applies, in particular, to determining the quantity of a cream marketed under the brand name Silkis™.

18 Claims, 3 Drawing Sheets

DEVICE TO ASSIST IN QUANTIFYING A PRODUCT AND ITS USE

The present invention relates to a device to assist in quantifying a product for application on the skin, and to its use. Such a product is, for example, a pharmaceutical or cosmetic composition.

More particularly, the invention relates to a device for correlating the percentage of body area affected with the quantity of a medicament intended for application on the skin.

In the field of medicaments intended for application on the skin, it is known that a good correlation between the quantity of product to be administered and the area of skin to be treated is important. Specifically, when the medicament intended for topical application is packaged in a tube or bottle, it is important for the practitioner to know exactly what quantity in grams, and therefore how many tubes, they should prescribe to their patient.

There are correlation tables available to doctors, but these are very often complex and impractical to use. Furthermore, the result of the correlation calculation gives a quantity in grams, for example, to be administered to the patient and does not allow the doctor to readily convert a quantity of product into a number of tubes to be prescribed for a given period of treatment. In particular, it has been shown that a certain number of doctors, especially dermatologists, do not give details of the quantity of medicaments for application.

Furthermore, even though each medicament is accompanied by information, this does not allow the practitioner to know how many tubes or bottles they should prescribe to the patient. Overdosing errors are possible, and may be detrimental to the patient.

In order to overcome the aforementioned drawbacks, the Applicant has now developed a device allowing the doctor to know exactly what maximum quantity, and therefore the number of tubes, they should prescribe to their patient, in particular for a treatment of four weeks, and as a function of the percentage of body area to be treated.

This object is achieved, according to a first object of the invention, by a device to assist in quantifying a medicament for application on the skin, characterised in that it includes, on the one hand, a first element having a first window and at least one additional window and, on the other hand, a second element having a first graduation and at least one additional graduation, each graduation comprising successive values, the said first and second elements being superimposed and mounted so as to rotate with respect to each other about an axis of rotation so that, when the second element is rotated with respect to the first element, each additional window is arranged in front of one of the successive values of each additional graduation, as a function of the position of the first window relative to the successive values of the first graduation.

The first and second elements are preferably flexible.

In practice, the first and second elements are mounted so as to rotate with respect to each other in particular by means of a rivet.

In the device according to the present invention, the number of graduations is equal to the number of windows.

The device of the invention is preferably of circular shape, and is in the form of a rotating disc which allows the doctor to correlate the percentage of body area affected with the quantity of product, in particular pharmaceutical or cosmetic products, intended for application on the skin.

The device according to the invention is preferably a rotating disc formed by assembling first and second elements which are positioned on one another, and which can rotate because of the central positioning of a rivet.

In such a device, the first and second elements are discs, respectively referred to as the upper disc and the lower disc, whose axis of rotation is positioned orthogonally to them and passes through their respective centres.

The discs are preferably made of paper, board or plastic.

Such a device is provided with a plurality of windows, also referred to as measuring windows, permitting a direct calculation to be carried out which allows the user to know exactly what quantity they should prescribe, and therefore how many tubes, and as a function of the percentage of body area to be treated.

There are at least two measuring windows present on the upper disc, or first element, which correspond to the first window and to at least one additional window. They can be positioned on values of graduations present on the second element, or lower disc, there being at least two of these graduations which corresponds to the first graduation and to at least one additional graduation.

The values of all the graduations are preferably inscribed circularly on the upper face of the second disc, which faces the first disc, while being centred on the axis of rotation. When the lower disc is rotated with respect to the upper disc, each additional window is arranged in front of one of the successive values of each corresponding additional graduation, as a function of the position of the first window relative to the successive values of the first graduation.

Preferably, the first graduation corresponds to the percentage of body surface affected by the disease and the additional graduations indicate the quantity of medicament, as well as the number of tubes to be prescribed.

Preferably, therefore, the device according to the invention comprises a first and a second element, the first element having a first window and at least one additional window and, on the other hand, the second element having a first graduation and at least one additional graduation, the values of the first graduation representing the severity of a dermatological disease from which a patient is suffering, and the values of at least one of the additional graduations, referred to as a second graduation, representing a maximum quantity of medicament to be prescribed for such a severity of disease.

The degree of a dermatological disease corresponds to the stage of this disease; it can be measured in particular as a percentage of body surface or as a body surface. The quantity of medicament can be measured, in particular, in units of weight such as grams or in units of volume, such as liters.

More preferably, the values of the first graduation indicate the percentage of body surface affected by the disease, and in that the values of at least one of the additional graduations, referred to as a second graduation, correspondingly indicate a maximum quantity of medicament to be prescribed for treating the patient, particularly in grams. More preferably, the successive values of at least one of the additional graduations, referred to as a second graduation, correspond to a quantity in grams corresponding to a treatment of four weeks.

The two categories of measuring windows, first and additional, on the rotating disc are advantageously arranged in relation to one another. The first window indicates the percentage of body surface to be treated, this percentage varying from 1% to 100% (these limits may vary according to the pathology to be treated). On the other side from this window, there is a series of additional windows, preferably at least two of them. These additional windows can be positioned on the successive values of an equal number of additional graduations, which correspond to the quantity of product as a function of the body surface to be treated, and to the number of tubes to be prescribed as a function of the quantity of product, which is itself a function of the body surface to be treated.

The device preferably comprises at least 3 graduations, preferably 3, and an equal number of corresponding windows, the values of the third graduation indicating the number of tubes necessary for treating a patient.

This number of tubes may be expressed differently as a function of the content of the tube. This content is preferably 30 g or 100 g.

More preferably, the device comprises 4 graduations and 4 corresponding windows, and the values of the third and fourth graduations respectively indicate the number of tubes with a first content, in particular 30 g, and the number of tubes with a second content, in particular 100 g, necessary for treating a patient.

A specific application of the device according to the invention relates to a medicament intended for treating psoriasis, the said medicament preferably being a cream or an ointment marketed by Galderma™ under the brand name Silkis™. Silkis™ is a medicament whose active principle is calcitriol.

In this case, the first measuring window indicates a percentage of body surface affected by psoriasis, this percentage being between 1 and 35%. A second measuring window makes it possible to calculate the maximum quantity in grams of Silkis™ necessary for treating a given body surface. Third and fourth measuring windows make it possible to know exactly how many 30 g and 100 g tubes of Silkis™ the doctor should prescribe to their patient. The maximum quantity in grams of Silkis™ determined by the disc corresponds to a treatment of four weeks.

The invention secondly relates to the use of the device according to the invention for evaluating the quantity of medicament, in particular Silkis™, necessary for treating a pathology, in particular psoriasis, over a given period, in particular four weeks.

Other advantages and characteristics of the invention will become apparent on reading the following example, which relates to a Silkis™ dosing device for the treatment of psoriasis, which is given by way of illustration and should not be interpreted as limiting the scope of the invention, and which refers to the appended figures in which.

Figure 1:
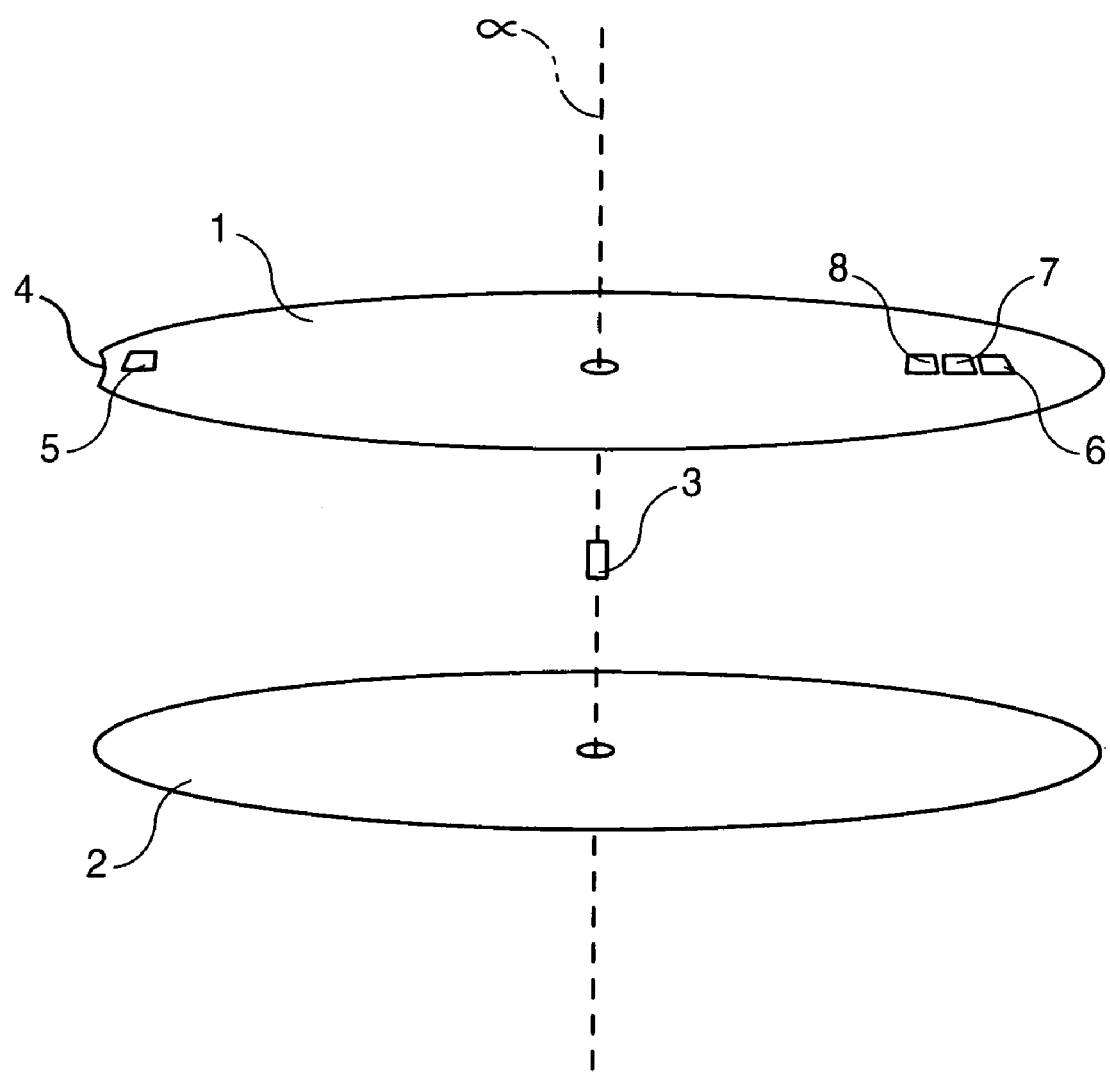
FIG. 1 represents an exploded view of the dosing device according to the invention.
Figure 2:
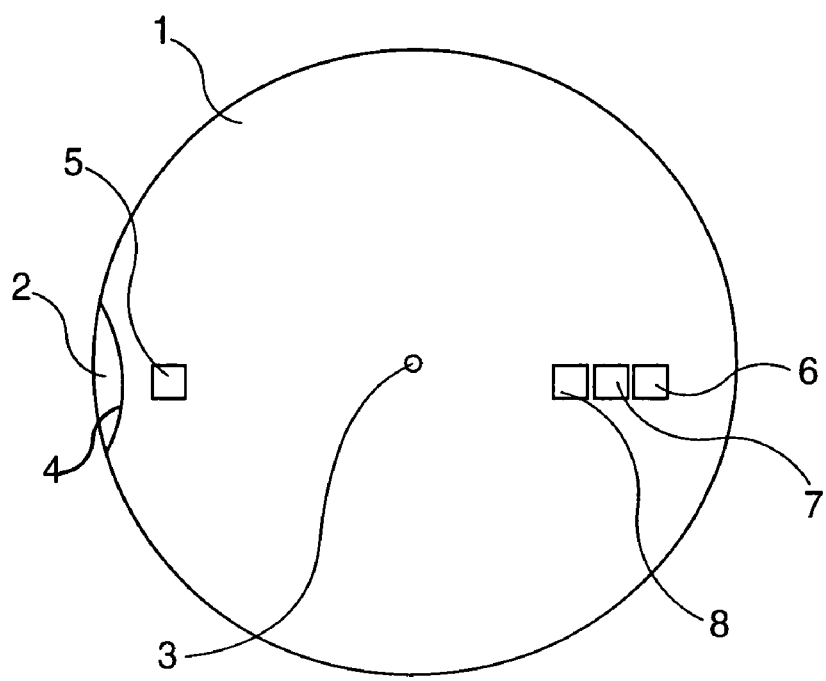
FIG. 2 represents a top view of the dosing device according to the invention.
Figure 3:
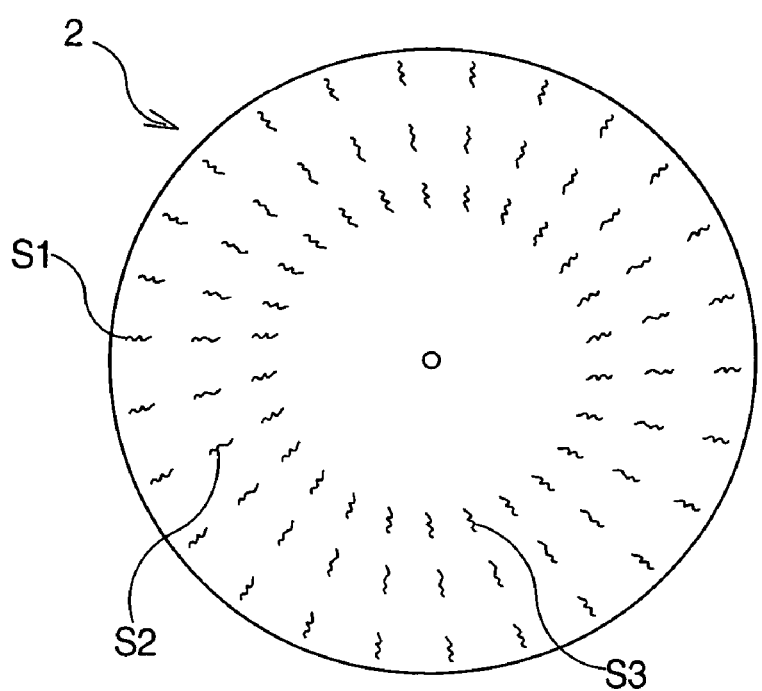
FIG. 3 represents a top view of the second disc of the device according to the invention.

FIGS. 1 and 2 represent a device according to the invention to assist in quantifying a product, consisting of a rotating disc formed by assembling two discs 1 and 2 on each other: assembly and rotation are facilitated by the central position of a rivet 3. Specifically, the lower disc 2 and the upper disc 1 are provided with a central opening for positioning a rivet, which assembles the two discs and allows the device to rotate.

The lower disc 2 (second element) advantageously has a radius of between 2 cm and 15 cm. On it, three series of numbers are arranged circularly above one another.

The first series S1 (first graduation), which is the furthest outwards, corresponds to various percentages of body surface affected by the disease. This percentage varies between 1 or 100% or less (percentages can vary according to the disease to be treated).

The second series S2 (second graduation) of numbers, which is further inwards, corresponds to the quantity in grams for treating the initially defined body surface for a specific treatment duration, in particular four weeks.

The last series S3 of numbers, which is the furthest inwards, corresponds to the number of tubes to be prescribed as a function of the quantity of product necessary for treating the affected area.

The upper disc 1 advantageously has a radius of between 2 cm and 15 cm.

Over a portion of the periphery of this disc, a notch 4 is formed to allow facilitated gripping and use of the device.

This disc furthermore has measuring windows which allows easy reading of the values inscribed on the lower disc.

These measuring windows will allow the users to precisely determine the maximum quantity in grams, as well as the number of tubes to be prescribed, for a treatment of four weeks.

There are three of these measuring windows. The first, lying immediately to the right of the notch, makes it possible to choose the percentage of body surface affected.

The second measuring window, lying 180° away from the first window, directly gives the maximum quantity in grams of product, for a given percentage of skin affected, necessary for a treatment of four weeks.

Further to the inside of the disc, beside the second measuring window, there is the third window which corresponds to the number of tubes of medicament which the practitioner should prescribe in order to obtain the quantity in grams necessary for treating the patient.

EXAMPLE

In the present example, the device makes it possible to quantify a medicament intended for treating psoriasis, the said medicament being Silkis™. The device is formed by assembling two discs, each with a radius of 70 mm. The discs are joined together by a rivet at the centre of the device.

On the lower disc, four series of numbers are inscribed and arranged above one another circularly. The first series of numbers corresponds to the percentage of body surface affected by psoriasis: this percentage varies from 1% to 35%. This percentage appears in the first measuring window 5 of the upper disc.

The second series of numbers, arranged further to the inside of the disc, makes it possible to know what maximum quantity in grams of Silkis™ which the doctor should prescribe to their patient, for a treatment of four weeks. This quantity is visible in the second measuring window 6 which the upper disc contains.

Two series of numbers, arranged even further to the inside of the disc, allow the doctor to know exactly how many 30 g tubes and 100 g tubes they should prescribe to their patient, for a treatment of four weeks. The number of tubes is indicated in the measuring windows 7 and 8 located on the upper disc.

Definition of the Body Surfaces to be Treated

In order to define the body surfaces to be treated in the context of treating psoriasis, the Applicant uses a proposal derived from the Wallace 9% rule ("Management guidelines for people with burn injury" NSW Health department, July 1996; "Magnitude of injury" T. E. Bowen and R. Bellamy, Emergency war surgery NATO handbook, 1998). The Applicant has thus determined the following percentages of body surface (expressed in relation to the total surface of the body):

inguinal fold: between abdomen and thigh=1%
gluteal fold=1% (3% of the back)
lumbar area=3% face=9%: 1% per ear, 1% per eyebrow, 1% chin, 1% per nasal fold, 2% forehead.

Determination of the Dose of Silkis™

Knowing that the maximum dose of Silkis™ usable per day is 30 g, in two applications, and that the maximum treatable body surface is 35% of the total surface of the body, the Applicant has established the optimum dose of Silkis™: 30/(2*35) i.e. 0.43 gram per percentage of body surface to be treated per application.

The following table summarises the correlation existing between the percentage of body surface to be treated and the quantity of Silkis™ to be administered, as well as the number of tubes to be prescribed, for a treatment period of four weeks.

|  | % of body surface | | | |
|---|---|---|---|---|
|  | 1% | 7% | 15% | 25% |
| Quantity of Silkis to be applied (in g) for four weeks of treatment | 24 g | 168 g | 361 g | 602 g |
| Number of 30 g Silkis ™ tubes | 1 | 0 | 2 | 0 |
| Number of 100 g Silkis tubes | 0 | 2 | 3 | 6 |

Use of the Disc to Assist in Quantifying Silkis™

Figure 4:
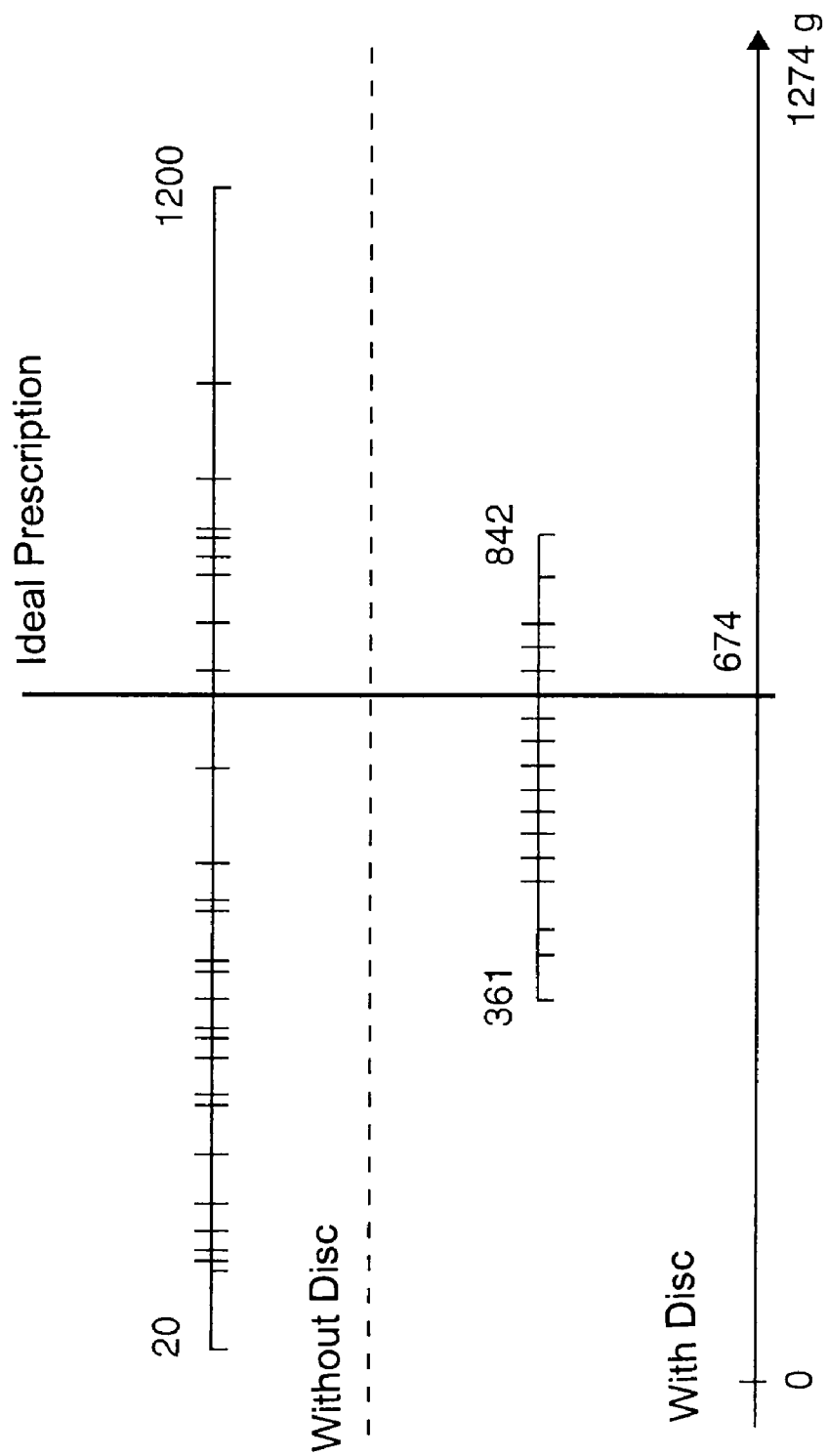
FIG. 4 is a graph comparing prescriptions made using the device according to the invention and without this device.

FIG. 4 represents, on a scale of from 0 to 1,274 g, the number of grams of Silkis™ prescribed to a patient for a treatment of four weeks, when 28% of the patient's body surface is affected by psoriasis.

When the treating doctors do not have the disc according to the invention, these doctors prescribe between 20 and approximately 1,200 g of Silkis™.

However, the prescription values in grams of Silkis™ are on average very far from the ideal prescription, which is 674 g.

If the doctors have a disc according to the invention, however, then they prescribe between 361 and 842 g of Silkis™. In this case, the prescription values in grams are on average very close to the aforementioned ideal value of 674 g.

By virtue of the disc according to the invention, therefore, the prescriptions are significantly more uniform and closer to the ideal prescription.

The invention claimed is:

1. A device to assist in quantifying a medicament for application on the skin, comprising:
   a first element including at least a first window and a second window; and
   a second element including at least a first graduation and a second graduation, each graduation having successive values,
   wherein the first and second elements are superimposed and mounted so as to rotate with respect to each other about an axis of rotation so that, when the second element is rotated with respect to the first element, the second window is arranged in front of the successive values of the second graduation, as a function of the position of the first window relative to the successive values of the first graduation, and
   wherein the successive values of the first graduation represent the severity of a dermatological disease, and the successive values of the second graduation represent a maximum quantity of medicament to be prescribed for such a corresponding severity of a dermatological disease.

2. The device according to claim 1, wherein the first and second elements are disc-shaped.

3. The device according to claim 2, wherein the axis of rotation is positioned orthogonally to the first and second elements and passes through a substantially central position of each of the first and second elements.

4. The device according to claim 1, wherein the first and second elements are flexible.

5. The device according to claim 1, wherein the first and second elements are mounted so as to rotate with respect to each other by means of a rivet.

6. The device according to claim 1, wherein the successive values of each graduation are inscribed circularly on an upper face of the second element, which faces the first element, while being centered on the axis of rotation.

7. The device according to claim 1, wherein the successive values of the first graduation indicate the percentage of body surface affected by the disease, and
   the successive values of the second graduation correspondingly indicate a maximum quantity of medicament in gams to be prescribed for treating a patient.

8. The device according to claim 7, wherein the first element further includes a third window,
   the second element further includes a third graduation, and
   the successive values of the third graduation indicate a number of tubes necessary for treating the patient.

9. The device according to claim 7, wherein the first element further includes a third window and a fourth window,
   the second element further includes a third graduation and a fourth graduation, and
   the successive values of the third and fourth graduations respectively indicate the number of tubes having first content, and the number of tubes having second content, necessary for treating a patient.

10. The device according to claim 9, wherein the first content is approximately 30 grams and the second content is approximately 100 grams.

11. The device according to claim 1, wherein the medicament is a medicament intended for treating psoriasis.

12. The device according to claim 11, wherein the medicament is Silkis™.

13. The device according to claim 11, wherein a percentage of body surface affected by psoriasis is between 1 and 35%.

14. The device according to claim 1, wherein the second element includes a plurality of graduations and the successive values of at least one of the plurality of graduations correspond to a quantity in grams of medicament corresponding to a treatment of four weeks.

15. The device according to claim 1, wherein the first element further includes a notch disposed on a side thereof for facilitating movement of the first element with respect to the second element.

16. The device according to claim 1, wherein the first graduation is inscribed radially furthest outwards on the second element, and
   wherein the second graduation is inscribed radially further inward on the second element with respect to the first graduation.

17. A method of quantifying a medicament for application on the skin, the method comprising:
   providing a device for quantifying a medicament, the device including:
      a first element having at least a first window and a second window, and a second element having at least a first graduation and a second graduation, each graduation having successive values; and using the device to evaluate the quantity of medicaments necessary for treating a pathology over a given period, wherein the first and second elements of the device are superimposed and mounted so as to rotate with respect to each other about an axis of rotation so that, when the second element is rotated with respect to the first element, the second window is arranged in front of the successive values of the second graduation, as a function of the position of the first window relative to the successive values of the first graduation, and wherein the successive values of the first graduation represent the severity of a dermatological disease, and the successive values of the second graduation represent a maximum quantity of medicament to be prescribed for such a corresponding severity of a dermatological disease.

18. The method according to claim 17, wherein the quantity of medicaments evaluated is a quantity of Silkis™ necessary for treating psoriasis for a period of four weeks.

* * * * *